(12) United States Patent
Anderson et al.

(10) Patent No.: US 6,265,591 B1
(45) Date of Patent: Jul. 24, 2001

(54) PROCESS FOR PREPARING 4-SUBSTITUTED-1H-INDOLE-3-GLYOXAMIDES

(75) Inventors: Benjamin Alan Anderson, Zionsville; Nancy Kay Harn, Indianapolis, both of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/647,471

(22) PCT Filed: Apr. 15, 1999

(86) PCT No.: PCT/US99/08332

§ 371 Date: Sep. 27, 2000

§ 102(e) Date: Sep. 27, 2000

(87) PCT Pub. No.: WO99/54300

PCT Pub. Date: Oct. 28, 1999

Related U.S. Application Data

(60) Provisional application No. 60/082,110, filed on Apr. 17, 1998.

(51) Int. Cl.[7] .................. C07D 209/12; C07D 209/14; C07D 209/30; C07D 209/34

(52) U.S. Cl. ................ 548/486; 548/491; 548/493; 548/494; 548/495

(58) Field of Search .................. 548/486, 491, 548/493, 494, 495

(56) References Cited

FOREIGN PATENT DOCUMENTS 0 675 110   4/1995  (EP) .
0 675 110 A1  *  4/1995  (EP) .

OTHER PUBLICATIONS

Draheim, et al., *Journal of Medicinal Chemistry,* Indole Inhibitors of Human Nonpancreatic Secretory Phospholipase A2. 3. Indole–3–Glyoxamides, vol. 39, No. 26, p. 5161, Scheme 2 (1996).

* cited by examiner

*Primary Examiner*—Jane C. Oswecki
(74) *Attorney, Agent, or Firm*—Francis O. Ginah; Arleen Palmberg

(57) ABSTRACT

A process for preparing 1H-indole-3-glyoxamides useful for inhibiting $SPLA_2$ and novel intermediates useful in the preparation of such compounds.

4 Claims, No Drawings

PROCESS FOR PREPARING 4-SUBSTITUTED-1H-INDOLE-3-GLYOXAMIDES

This application is a 371 of PCT/US99/08332 filed Apr. 15, 1999, which claims benefit of U.S. Provisional Application No. 60/082,110 filed Apr. 17, 1998.

This invention relates to a process for preparing certain 1H-indole-3-glyoxamides useful for inhibiting sPLA$_2$ mediated release of fatty acids for conditions such as septic shock and intermediates useful in the preparation of such compounds.

Certain 1H-indole-3-glyoxamides are known to be potent and selective inhibitors of mammalian sPLA$_2$ useful for treating diseases, such as septic shock, adult respiratory distress syndrome, pancreatitis, trauma, bronchial asthma, allergic rhinitis, rheumatoid arthritis and related sPLA$_2$ induced diseases. EPO publication No. 0675110, for example, discloses such compounds.

Various patents and publications describe processes for making these compounds using 4-hydroxy indole intermediates.

The article, "Recherches en serie indolique. VI sur tryptamines substituees", by Marc Julia, Jean Igolen and Hanne Igolen, *Bull. Soc. Chim. France*, 1962, pp. 1060–1068, describes certain indole-3-glyoxylamides and their conversion to tryptamine derivatives.

The article, "2-Aryl-3-Indoleglyoxylamides (FGIN-1): A New Class of Potent and Specific Ligands for the Mitochondrial DBI Receptor (MDR)" by E. Romeo, et al., *The Journal of Pharmacology and Experimental Therapeutics*, Vol. 262, No. 3, (pp. 971–978) describes certain 2-aryl-3-indolglyoxylamides having research applications in mammalian central nervous systems.

The abstract, "Fragmentation of N-benzylindoles in Mass Spectrometry"; Chemical Abstracts, Vol. 67, 1967, 73028h, reports various benzyl substituted phenols including those having glyoxylamide groups at the 3 position of the indole nucleus.

U.S. Pat. No. 3,449,363 describes trifluoromethylindoles having glyoxylamide groups at the 3 position of the indole nucleus.

U.S. Pat. No. 3,351,630 describes alpha-substituted 3-indolyl acetic acid compounds and their preparation inclusive of glyoxylamide intermediates.

U.S. Pat. No. 2,825,734 describes the preparation of 3-(2-amino-1-hydroxyethyl)indoles using 3-indoleglyoxylamide intermediates such as 1-phenethyl-2-ethyl-6-carboxy-N-propyl-3-indoleglyoxylamide (see, Example 30).

U.S. Pat. No. 4,397,850 prepares isoxazolyl indolamines using glyoxylamide indoles as intermediates. U.S. Pat. No. 3,801,594 describes analgesics prepared using 3-indoleglyoxylamide intermediates.

The article, "No. 565. —Inhibiteurs d'enzymes. XII.— Preparation de (propargylamino-2 ethyl)-3 indoles" by A. Alemanhy, E. Fernandez Alvarez, O. Nieto Lopey and M. E. Rubio Herraez; *Bulletin De La Societe Chimigue De France*, 1974, No. 12, pp. 2883–2888, describes various indolyl-3 glyoxamides which are hydrogen substituted on the 6-membered ring of the indole nucleus.

The article "Indol-Umlagerung von 1-Diphenylamino-2,3-dihydro-2,3-pyrrolidonen" by Gert Kollenz and Christa Labes; *Liebigs Ann. Chem.*, 1975, pp. 1979–1983, describes phenyl substituted 3-glyoxylamides.

Many of these processes employ a 4-hydroxy indole intermediate. For example U.S. Pat. No. 5,654,326 U.S., herein incorporated by reference in its entirety, discloses a process for preparing 4-substituted-1H-indole-3-glyoxamide derivatives comprising reacting an appropriately substituted 4-methoxyindole (prepared as described by Clark, R. D. et al., *Synthesis*, 1991, pp 871–878, the disclosures of which are herein incorporated by reference) with sodium hydride in dimethylformamide at room temperature (20–25° C.) then treating with arylmethyl halide at ambient temperatures to give the 1-arylmethylindole which is O-demethylated using boron tribromide in methylene chloride (Tsung-Ying Shem and Charles A. Winter, *Adv. Drug Res.*, 1977, 12, 176, the disclosure of which is incorporated by reference) to give the 4-hydroxyindole. Alkylation of the hydroxy indole is achieved with an alpha bromoalkanoic acid ester in dimethylformamide using sodium hydride as a base. Conversion to the glyoxamide is achieved by reacting the α-[(indol-4-yl)oxy]alkanoic acid ester first with oxalyl chloride, then with ammonia, followed by hydrolysis with sodium hydroxide in methanol.

The process for preparing 4-substituted-1H-indole-3-glyoxamide derivatives, as set forth above, has utility. However, this process uses expensive reagents and environmentally hazardous organic solvents, produces furan containing by-products and results in a relatively low yield of desired product.

In an alternate preparation an appropriately substituted proprionylacetate is halogenated with sulfuryl chloride. The halogenated intermediate is hydrolyzed and decarboxylated by treatment with hydrochloric acid then reacted with an appropriately substituted cyclohexane dione. Treatment of the alkylated dione with an appropriate amine affords a 4-keto-indole which is oxidized by refluxing in a high-boiling polar hydrocarbon solvent such as carbitol in the presence of a catalyst, such as palladium on carbon, to prepare the 4-hydroxyindole which may then be alkylated and converted to the desired glyoxamide as described above.

This process however is limited by the required high temperature oxidation and requires recovery of a precious metal catalyst. While the methods described above for preparing the 4-hydroxy indole intermediate are satisfactory, a more efficient transformation is desirable.

The present invention provides an improved process for preparing 1H-indole-3-glyoxamides. The process of the present invention can be performed with inexpensive, readily available, reagents under milder conditions and resulting in better overall yield. In addition, the present process allows for transformation with a wider variety of substituents on the indole platform. Other objects, features and advantages of the present invention will become apparent from the subsequent description and the appended claims.

The present invention provides a process for preparing a compound of the formula I or a pharmaceutically acceptable salt or prodrug derivative thereof;

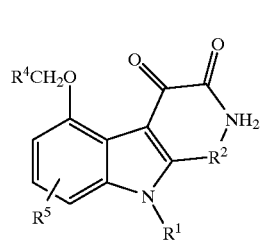

(I)

wherein:

R¹ is selected from the group consisting of $C_7$–$C_{20}$ alkyl;

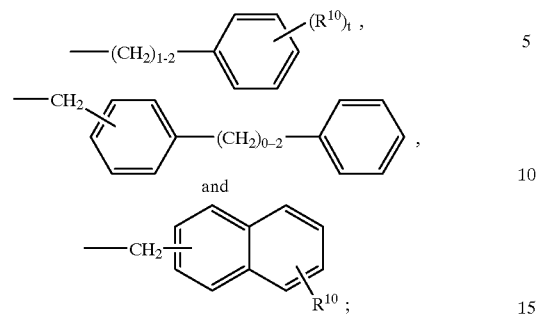
and wherein;

$R^{10}$ is selected from the group consisting of halo, $C_1$–$C_{10}$ alkyl, $C_1$–$C_{10}$ alkoxy, —S—($C_1$–$C_{10}$ alkyl) and halo($C_1$–$C_{10}$)alkyl, and t is an integer from 0 to 5 both inclusive;

$R^2$ is selected from the group consisting of hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), aryl, aryloxy, and HET;

R4 is selected from the group consisting of —$CO_2H$, —$SO_3H$, and —P(O) $(OH)_2$ or salt or prodrug derivatives thereof; and $R^5$ is selected from the group consisting of hydrogen, ($C_1$–$C_6$)alkyl, ($C_1$–$C_6$)alkoxy, halo($C_1$–$C_6$)alkoxy, halo($C_2$–$C_6$)alkyl, bromo, chloro, fluoro, iodo and aryl;

which process comprises the steps of:

a) halogenating a compound of formula X

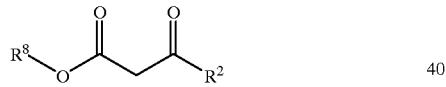

where $R^8$ is ($C_1$–$C_6$)alkyl, aryl or HET;
with $SO_2Cl_2$ to form a compound of formula IX

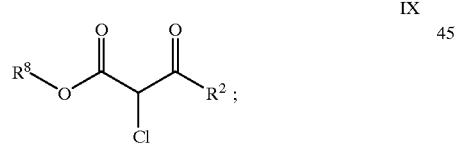

b) hydrolyzing and decarboxylating a compound of formula IX

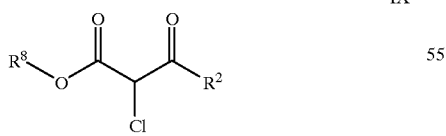

to form a compound of formula VIII

c) alkylating a compound of formula VII

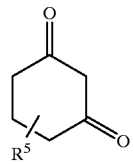

with a compound of formula VIII

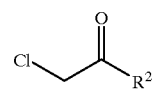

to form a compound of formula VI

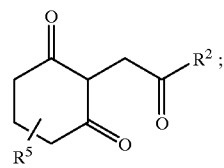

d) aminating and dehydrating a compound of formula VI

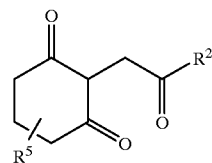

with an amine of the formula $R^1NH_2$ in the presence of a solvent that forms an azeotrope with water to form a compound of formula V

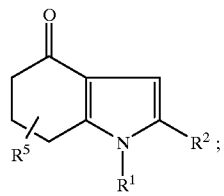

e) oxidizing a compound of formula V

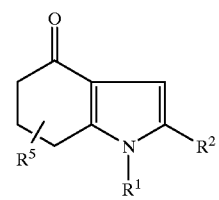

by heating with a base and a compound of the formula RSOX where R is —($C_1$–$C_6$) alkyl or aryl and X is —(C₁–C₆)alkoxy, halo or —OCO₂(C₁–C₆)alkyl to form a compound of formula IV

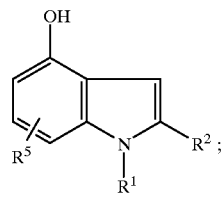

IV f) alkylating a compound of the formula IV

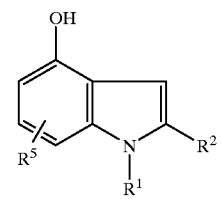

IV with an alkylating agent of the formula XCH₂R^{4a} where X is a leaving group and R^{4a} is —CO₂R^{4b}, —SO₃R^{4b}, —P(O)(OR^{4b})₂, or —P(O)(OR^{4b})H, where R^{4b} is an acid protecting group, to form a compound of formula III

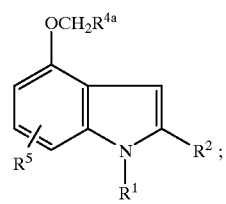

III g) reacting a compound of formula III

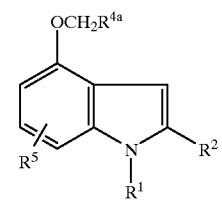

III with oxalyl chloride and ammonia to form a compound of formula II

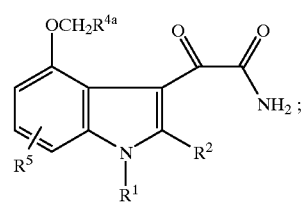

II h) optionally hydrolyzing a compound of formula II

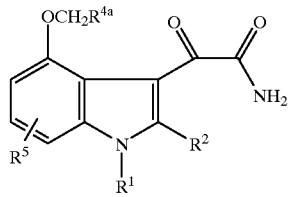

II to form a compound of formula I; and i) optionally salifying a compound of formula I.

In another embodiment of the invention is provided a process for preparing a compound of formula I comprising the steps of:

a) oxidizing a compound of the formula V

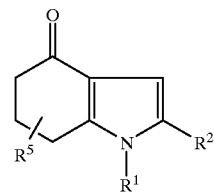

V by heating with a base and a compound of the formula RSOX where R is —(C₁–C₆)alkyl or aryl and X is —(C₁–C₆)alkoxy, halo or —OCO₂(C₁–C₆)alkyl to form a compound of formula IV

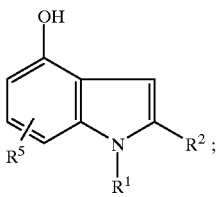

IV b) alkylating a compound of the formula IV

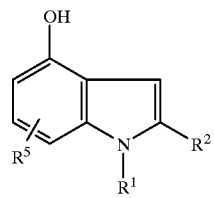

IV with an alkylating agent of the formula XCH₂R^{4a} where X is a leaving group and R^{4a} is —CO₂R^{4b}, —SO₃R^{4b}, —P(O)(OR^{4b})₂, or —P(O)(OR^{4b})H, where R^{4b} is an acid protecting group, to form a compound of formula III c) reacting a compound of formula III

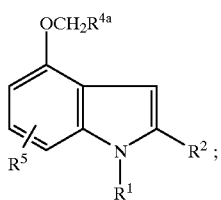

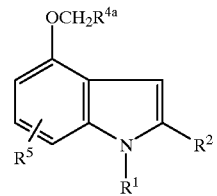

with oxalyl chloride and ammonia to form a compound of formula II

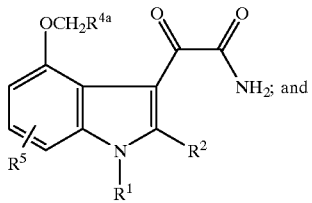

d) optionally hydrolyzing a compound of formula II

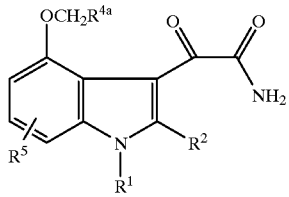

to form a compound of formula I; and
e) optionally salifying a compound of formula I.

The compounds of the invention employ certain defining terms as follows:

As used herein, the term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, tert-butyl, n-pentyl, isopentyl, neopentyl, heptyl, hexyl, octyl, nonyl, decyl, and the like.

The term "($C_1$–$C_{10}$) alkoxy", as used herein, denotes a group such as methoxy, ethoxy, n-propoxy, isopropoxy, n-butoxy, t-butoxy, n-pentoxy, isopentoxy, neopentoxyl, heptoxy, hexoxy, octoxy, nonoxy, decoxy and like groups, attached to the remainder of the molecule by the oxygen atom.

The term "($C_3$–$C_4$) cycloalkyl" includes cyclopropyl, and cyclobutyl groups

The term "C3–C4 cycloalkenyl" includes a cyclopropenyl or cyclobutenyl ring having a double bond at the 1- or 2-position.

The term "halo" means fluoro, chloro, bromo or iodo.

The term "halo($C_1$–$C_{10}$)alkyl" means a ($C_1$–$C_{10}$)alkyl group, substituted with from 1 to 3 halo atoms, attached to the remainder of the molecule by the alkyl group. The term halo($C_1$–$C_{10}$)alkyl includes the term halo($C_2$–C6)alkyl.

The term "halo($C_1$–$C_6$)alkoxy" means a halo-substituted alkoxy group which group is attached to the remainder of the molecule at the oxygen of the alkoxy.

The term "aryl" means a group having the ring structure characteristic of benzene, pentalene, indene, naphthalene, azulene, heptalene, phenanthrene, anthracene, etc. The aryl group may be optionally substituted with 1 to 3 substituents selected from the group consisting of ($C_1$–$C_6$)alkyl (preferably methyl), ($C_1$–$C_6$)alkoxy or halo (preferable fluorine or chlorine).

The term "aryloxy" means an aryl group attached to the remainder of the molecule by an oxygen linker.

The term "leaving group" means a substituent with an unshared electron pair that departs from the substrate in a nucleophilic substitution reaction. The term "leaving group" includes halo, sulfonate, acetate and the like.

The term HET includes pyridine, pyrazine, pyrimidine, pyridazine, pyrrole, pyrazole, furan, thiophene, thiazole, isothiazole, oxadiazole, thiadiazole, imidazole, triazole and tetrazole. The heterocyclic ring can be attached to the remainder of the molecule by any carbon in the heterocyclic ring.

The salts of the compounds of formula I are an additional aspect of the invention. In those instances where the compounds of the invention possess acidic functional groups various salts may be formed which are more water soluble and physiologically suitable than the parent compound. Representative pharmaceutically acceptable salts include but are not limited to the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.,* 66: 1–19 (1977)).

The term "acid protecting group" is used herein as it is frequently used in synthetic organic chemistry, to refer to a group which will prevent an acid group from participating in a reaction carried out on some other functional group of the molecule, but which can be removed when it is desired to do so. Such groups are discussed by T. W. Greene in chapter 5 of *Protective Groups in Organic Synthesis,* John Wiley and Sons, New York, 1981, incorporated herein by reference in its entirety.

Examples of acid protecting groups includes ester or amide derivatives of the acid group, such as methyl, methoxymethyl, methyl-thiomethyl, tetrahydropyranyl, methoxyethoxymethyl, benzyloxymethyl, phenylaryl, ethyl, 2,2,2-trichloroethyl, 2-methylthioethyl, t-butyl, cyclopentyl, triphenylmethyl, p-bromobenzyl, trimethylsilyl, N,N-dimethyl, pyrrolidinyl, piperidinyl or o-nitroanilide. A preferred acid-protecting group is methyl.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives, such as, esters prepared by reaction of the parent acidic compound with a suitable alcohol, or amides prepared by reaction of the parent acid compound with a suitable amine. Simple aliphatic esters (e.g., methyl, ethyl, propyl, isopropyl, butyl, sec-butyl, tert-butyl) or aromatic esters derived from acidic groups pendent on the compounds of this invention are preferred prodrugs. Other preferred esters include morpholinoethyloxy, diethylglycolamide and diethylaminocarbonylmethoxy In some cases it is desirable to prepare double ester type prodrugs such as (acyloxy) alkyl esters or ((alkoxycarbonyl)oxy)alkyl esters.

A preferred group of compounds of formula I prepared by the process of the instant invention are those wherein:

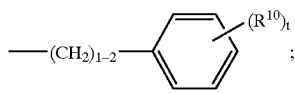

$R^1$ is $R^2$ is halo, cyclopropyl, methyl, ethyl, propyl, O-methyl or S-methyl;

$R^4$ is —CO$_2$H; and $R^5$, $R^6$ and $R^7$ are H.

Compounds which can be made by the process of the instant invention include:

((3-(2-amino-1,2-dioxyethyl)-2-methyl-1-(phenylmethyl)-1H-indol-4-yl)oxy)acetic acid;
dl-2-((3-(2-amino-1,2-dioxyethyl)-2-methyl-1-(phenylmethyl)-1H-indol-4-yl)oxy)propanoic acid;
((3-(2-amino-1,2-dioxyethyl)-1-(((1,1'-biphenyl)-2-ylmethyl)-2-methyl-1H-indol-4-yl)oxy)acetic acid;
((3-(2-amino-1,2-dioxyethyl)-1-((1,1'-biphenyl)-3-ylmethyl)-2-methyl-1H-indol-4-yl)oxy)acetic acid;
((3-(2-amino-1,2-dioxyethyl)-1-((1,1'-biphenyl)-4-ylmethyl)-2-methyl-1H-indol-4-yl)oxy) acetic acid;
((3-(2-amino-1,2-dioxyethyl)-1-((2,6-dichlorophenyl)methyl)-2-methyl-1H-indol-4-yl)oxy) acetic acid;
((3-(2-amino-1,2-dioxyethyl)-1-(4-fluorophenyl)methyl)-2-methyl-1H-indol-4-yl)oxy)acetic acid;
((3-(2-amino-1,2-dioxyethyl)-2-methyl-1-((naphthalenyl)methyl)-1H-indol-4-yl)oxy)acetic acid;
((3-(2-amino-1,2-dioxyethyl)-2-ethyl-1-(phenylmethyl)-1H-indol-4-yl)oxy)acetic acid;
((3-(2-amino-1,2-dioxyethyl)-1-((3-chlorophenylmethyl)-2-ethyl-1H-indol-4-yl)oxy)acetic acid;
((3-(2-amino-1,2-dioxyethyl)-1-((1,1'biphenyl)-2-ylmethyl)-2-ethyl-1H-indol-4-yl)oxy)acetic acid;
((3-(2-amino-1,2-dioxyethyl)-1-((1,1'-biphenyl)-2-ylmethyl)-2-propyl-1H-indol-4-yl)oxy)acetic acid;
((3-(2-amino-1,2-dioxyethyl)-2-cyclopropyl-1-(phenylmethyl)-1H-indol-4-yl)oxy)acetic acid;
((3-(2-amino-1,2-dioxyethyl)-1-((1,1'biphenyl)-2-ylmethyl)-2-cyclopropyl-1H-indol-4-yl)oxy)acetic acid;
4-((3-(2-amino-1,2-dioxyethyl)-2-ethyl-1-(phenylmethyl)-1H-indol-4-yl)oxy)butanoic acid;
((3-(2-amino-1,2-dioxyethyl)-2-ethyl-1-(phenylmethyl)-1H-indol-4-yl)oxyacetic acid;
((-3-(2-amino-1,2-dioxyethyl)-2-ethyl-6-methyl-1-(phenylmethyl)-1H-indol-4-yl)oxy)acetic acid;
((-3-(2-amino-1,2-dioxyethyl)-2,6-dimethyl-1-(phenylmethyl)-1H-indol-4-yl)oxy)acetic acid;
((3-(2-amino-1,2-dioxyethyl)-2-methyl-1-(phenylmethyl)-1H-indol-4-yl)oxy)acetic acid;
((3-(2-amino-1,2-dioxyethyl)-6-ethyl-2-methyl-1-(phenylmethyl)-1H-indol-4-yl)oxy)acetic acid;
((3-(2-amino-1,2-dioxyethyl)-2,6-diethyl1-(phenylmethyl)-1H-indol-4-yl)oxy)acetic acid;
((3-(2-amino-1,2-dioxyethyl)-2-methyl-6-phenoxy-1-(phenylmethyl)-1H-indol-4-yl)oxy)acetic acid;
((3-(aminooxoacetyl)-2-ethyl-6-methyl-1-(phenylmethyl)-1H-indol-4-yl)oxy)acetic acid; and
((3-(2-amino-1,2-dioxyethyl)-2-ethyl-6-phenoxy-1-(phenylmethyl)-1H-indol-4-yl)oxy)acetic acid or a pharmaceutically acceptable salt thereof.

Of these compounds, preferred compounds include:

((3-(2-amino-1,2-dioxyethyl)-2-ethyl-1-(phenylmethyl)-1H-indol-4-yl)oxyacetic acid;
((-3-(2-amino-1,2-dioxyethyl)-2-ethyl-6-methyl-1-(phenylmethyl)-1H-indol-4-yl)oxy)acetic acid;
((-3-(2-amino-1,2-dioxyethyl)-2,6-dimethyl-1-(phenylmethyl)-1H-indol-4-yl)oxy)acetic acid;
((3-(2-amino-1,2-dioxyethyl)-2-methyl-1-(phenylmethyl)-1H-indol-4-yl)oxy)acetic acid;
((3-(2-amino-1,2-dioxyethyl)-6-ethyl-2-methyl-1-(phenylmethyl)-1H-indol-4-yl)oxy)acetic acid;
((3-(2-amino-1,2-dioxyethyl)-2,6-diethyl-1-(phenylmethyl)-1H-indol-4-yl)oxy)acetic acid;
((3-(2-amino-1,2-dioxyethyl)-2-methyl-6-phenoxy-1-(phenylmethyl)-1H-indol-4-yl)oxy)acetic acid;
((3-(aminooxoacetyl)-2-ethyl-6-methyl-1-(phenylmethyl)-1H-indol-4-yl)oxy)acetic acid; and
((3-(2-amino-1,2-dioxyethyl)-2-ethyl-6-phenoxy-1-(phenylmethyl)-1H-indol-4-yl)oxy)acetic acid or a pharmaceutically acceptable salt thereof.

Of these compounds even more preferred are:
((3-(2-amino-1,2-dioxyethyl)-2-methyl-1-(phenylmethyl)-1H-indol-4-yl)oxy)acetic acid and ((3-(2-amino-1,2-dioxyethyl)-2-ethyl-1-(phenylmethyl)-1H-indol-4-yl) oxyacetic acid.

The most preferred compound which can be prepared by the instant process is ((3-(2-amino-1,2-dioxyethyl)-2-ethyl-1-(phenylmethyl)-1H-indol-4-yl)oxyacetic acid or a pharmaceutically acceptable salt thereof.

The process of the present invention provides an improved method for synthesizing the compounds of formula I using inexpensive, readily available reagents as shown in Scheme I as follows.

Scheme I

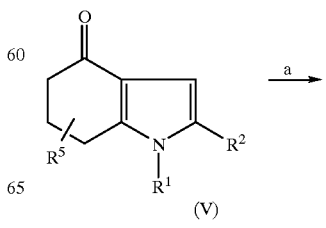

(V)

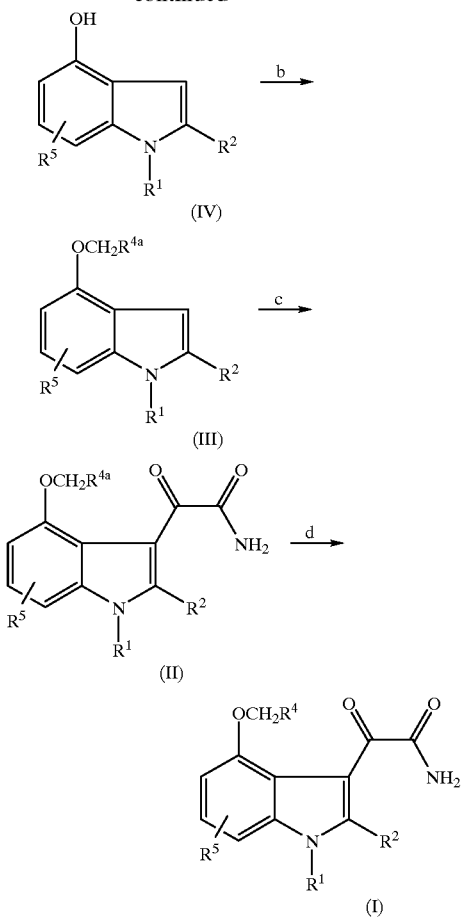

Ketone (V) is dissolved in a suitable solvent preferably an aprotic solvent such as THF. Other suitable solvents include but are not limited to DMF, dioxane, or toluene. The substrate/solvent solution may be sonicated or heated slightly, if necessary to facilitate dissolution.

The amount of solvent used should be sufficient to ensure that all compounds stay in solution until the desired reaction is complete.

The solution is treated with a base, preferably a strong base such as sodium hydride, then with a sulfinating agent of the formula

where R is —$(C_1-C_6)$alkyl, aryl or substituted aryl and X is $(C_1-C_6)$alkoxy, halo or —$OCO_2(C_1-C_6)$alkyl. The sulfinating reagent may be prepared according to the procedure of J. W. Wilt et al., *J. Org. Chem*, 1967, 32, 2097. Preferred sulfinating agents include methyl p-tolyl sulfinate, methylbenzene sulfinate or p-toluylsulfinic isobutyric anhydride. Other suitable bases include but are not limited to LDA, sodium methoxide, or potassium methoxide. Preferably two equivalents of base are used. Preferably, when sodium hydride is employed, the base is added before the sulfinating reagent. The order of addition of reagents is not important when sodium methoxide is used.

The reaction may be conducted at temperatures from about 25° C. to reflux, preferably at reflux and is substantially complete in from one to 24 hours.

The amount of sulfinating reagent is not critical, however, the reaction is best accomplished using a molar equivalent or excess relative to the pyrrole starting material (1).

The above reactions may be run as a "one pot" process with the reactants added to the reaction vessel in the order given above.

Dioxane is a preferred solvent in a "one part" process. THF and toluene, respectively, are preferred solvents if a "two pot" process is employed as depicted in scheme I(a), below.

The intermediates IV can be isolated and purified using standard crystallization or chromatographic procedures.

Standard analytical techniques such as TLC or HPLC can be used to monitor the reactions in order to determine when the starting materials and intermediates are converted to product.

In an alternate preparation, the sulfinating reagent can be replaced with a disulfide compound of the formula $R^{20}SSR^{20}$ where $R^{20}$ is alkyl or aryl. Oxidation of the sulfide intermediate can then be readily achieved using an appropriate oxidizing reagent such as hydrogen peroxide or m-chloroperbenzoic acid.

Indole (IV) may then be readily alkylated with an alkylating agent of the formula $XCH_2R^{4a}$ where X is a suitable leaving group and $R^{4a}$ is a protected carboxy, sulfonyl or phosphonyl acid group, preferably protected with an ester group, in the presence of a base. Methyl bromoacetate is a preferred alkylating agent. Suitable bases include potassium carbonate, sodium carbonate, lithium carbonate, cesium carbonate, sodium bicarbonate, potassium bicarbonate or potassium hydroxide. Potassium carbonate is preferred. The amount of alkylating agent is not critical, however, the reaction is best accomplished using a molar excess of alkylating agent relative to the starting material. The reaction is preferably carried out in an organic solvent such as acetone, acetonitrile or dimethylformanide. Other suitable solvents include tetrahydrofuran, methyl ethyl ketone, acetonitrile, toluene, or t-butyl methylether. The reaction is conducted at temperatures of from about 0° to 100° C., preferably at ambient temperature, and is substantially complete in about 1 to 24 hours depending on the reactants employed and such conditions as reaction temperature.

Optionally, a phase transfer reagent such as tetrabutylammoniumbromide may be employed.

Preparation of glyoxamide II is readily achieved in a two step process by first treating intermediate III with oxalyl chloride at concentrations from about 0.2 to 1.5 mmol, preferably at equimolar concentrations relative to the starting material. Solvents such as methylene chloride, chloroform, trichloroethylene, carbon tetrachloride, ether or toluene are preferred. Temperatures from about −20° C. to ambient temperature are suitable, preferably about −5° C.

In the second step, the solution is treated with ammonia; either bubbled in as a gas or, preferably, using a molar excess of 30% aqueous ammonia. The reaction is typically conducted at temperatures from about −25° C. to 25° C., preferably at about −2° C. to 0° C., and is substantially complete in 10 minutes to an hour.

Hydrolysis of II is achieved using a base such as potassium hydroxide, lithium hydroxide or sodium hydroxide, preferably sodium hydroxide, in a lower alcohol solvent, such as methanol, ethanol, isopropanol, etc., or solvents such as tetrahydrofuran, dioxane and acetone.

Using standard analytical techniques, such as HPLC, the reactions of Scheme I can be monitored to determine when starting materials and intermediates are converted to product.

Scheme I(a), below, illustrates the two pot procedure, described above, for the preparation of intermediate IV. Intermediate IV(a) can be isolated and purified using standard chromatographic procedures.

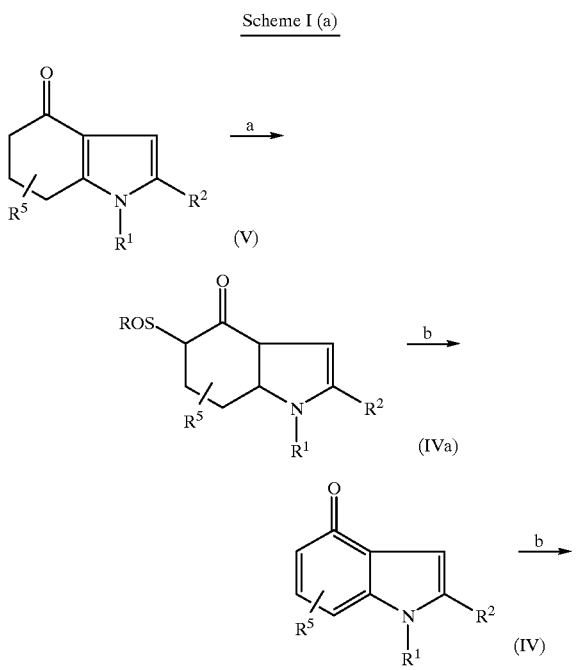

It will be readily appreciated by the skilled artisan that the starting materials for the above procedures are either commercially available or can be readily prepared by known techniques from commercially available starting materials. For example, the sulfinating and sulfinylating reagents can be made according to the procedure of Patai, et al. The chemistry of sulphinic acids, ester and their derivatives; John Wiley and sons, 1990 p.217–236 & 557–600.

Starting material V is prepared according to the following procedure.

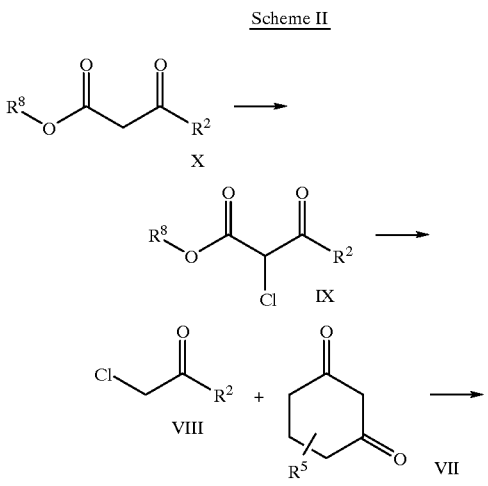

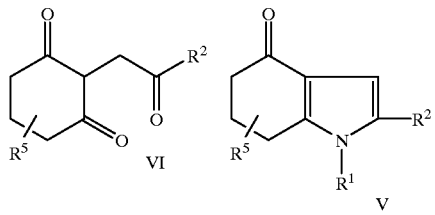

$R^8$ is ($C_1$–$C_6$) alkyl or aryl.

An appropriately substituted propionylacetate X is first halogenated by treatment with sulfuryl chloride, preferably at equimolar concentrations relative to the starting material, at temperatures of from about 0° C. to 25° C., preferably less than 15° C., to prepare IX.

Hydrolysis and decarboxylation of IX is achieved by refluxing with an aqueous acid, such as hydrochloric acid, for from about 1 to 24 hours. The solution containing the decarboxylated product VIII is neutralized to adjust the pH to about 7.0–7.5, then reacted with cyclohexanedione VII (preferably at equimolar concentrations) and a base, preferably sodium hydroxide, to yield the triketone monohydrate VI as a precipitate which may be purified and isolated, if desired. The reaction is preferably conducted at temperatures of from −20° C. to ambient temperatures and is substantially complete in about 1 to 24 hours.

The above reactions are preferably run as a "one pot" process with the reactants added to the reaction vessel in the order given above. Preferably, the reaction is allowed to proceed without isolating compounds of formula IX or VIII, thus avoiding exposure to these volatile lachrymators.

Preparation of V is achieved by refluxing VI in a high boiling non-polar solvent which forms an azeotrope with water, preferably toluene, with an equimolar quantity of an amine of the formula $R^1NH_2$, where $R^1$ is as defined above.

Solvents with a boiling point of at least 100° C. are preferred, such as toluene, xylene, cymene, benzene, 1,2-dichloroethane or mesitylene, thus eliminating the need for a pressure reactor. Sufficient solvent should be employed to ensure that all compounds stay in solution until the reaction is substantially complete in about 1 to 24 hours.

The following examples further illustrate the process of the present invention. The examples also illustrate the preparation of the intermediate compounds of this invention. The examples are illustrative only and not intended to limit the scope of the invention in any way.

EXAMPLE 1

Preparation of ((2-ethyl-1-(phenylmethyl)-1H-indol-4-yl)oxy)acetic acid methyl ester A. Preparation of 2-(2-oxobutyl)-1,3-cyclohexanedione 1-Benzyl-2-ethyl-4-oxo-4,5,6,7-tetrahydroindole (1000 gms, 4.995 moles) was suspended in toluene (6000 ml, 6 vol). The mixture was warmed to 85 deg c and stirred for 5 minutes. Benzylamine (562.6 gms, 5.25 moles, 1.05 eq) was added dropwise over ~30–45 minutes. Following the addition the mixture turned to an amber colored solution. Heat was applied to the solution and water was azeotroped off until the reaction temperature reached 110 C.°. The reaction was allowed to stir at 110 C.° for 2 hrs at which time ~4000 mls of solvent was distilled off at atmospheric pressure. Solution was transferred to a flask and further evaporated to an amber viscous oil which was used directly in the following step.

oil wt=1372.24 gms
Theoretical wt=1253.7 gms
Potency=87%
Molar yield=95.2%

B. Preparation of 2-ethyl-(phenylmethyl)-1H-indol-4-ol

Sodium hydride (400 gms, 9.96 moles, 2.5 eq) was suspended in THF (5000 mls, 5 vol). To the suspension was added the compound of part A, above, (1149 gms, 3.98 moles, 1eq) and allowed to stir at 20–25 deg c until bubbling had subsided. Methyl toluene sulfinate (1121 gms, 6.59 moles, 1.65 eq) was added and the mixture was heated to 30 C.°. After ~2.5 hrs, the mixture darkened as gas evolution and an exotherm to 47 deg c was observed. TLC indicated complete consumption of starting material. The reaction was then cooled to 0 to 5 C.° and quenched with the slow addition of deionized water (5000 mls, 5 vol). The reaction was further quenched with glacial acetic acid (600 gms, 10 moles, 2.5 eq). The mixture was diluted with toluene (5000 mls, 5 vol) and washed with saturated sodium bicarbonate (2500 mls, 2.5 vol). The upper organic layer was washed with and additional 2500 mls of saturated sodium bicarbonate. The aqueous layers were combined and backextracted with toluene (5000 mls, 5 vol). The organic layers were combined and heated to a gentle reflux (~80 deg c) and stirred for 2 hrs, at which time reaction completion was confirmed by TLC. The dark solution was concentrated atmospherically to ~4000 mls and washed with saturated sodium bicarbonate (1500 mls×2). The organic was dried over magnesium sulfate and was concentrated under vacuum to a dark viscous oil which was used directly in the following step.

C. Preparation of ((2-ethyl-1-(phenylmethyl)-1H-indol-4-yl)oxy)acetic acid methyl ester The compound of part B, above, was dissolved in acetone (7500 mls, 7.5 vol) and stirred at 20 to 25 deg c. Powdered potassium carbonate (1360 gms, 9.84 moles, 2.5 eq) and methylbromoacetate (780 gms, 5.09 moles, 1.3 eq) were added and the tan mixture was allowed to stir for 16 hrs at 20 to 25 C.°, at which time, reaction completion was confirmed by TLC. The solids were filtered over polypropylene and washed with acetone (1500 mls, 1.5 vol) The filtrate was evaporated, under vacuum, to a dark oil. The oil was dissolved in isopropyl alcohol (10,000 mls, 10 vol ) and the resulting slurry was heated to reflux for 30 minutes. The solution was allowed to self cool with crystallization occurring at ~38 C.°. The slurry was cooled to 0 to 5 C.° and stirred for 2 hrs. The slurry was filtered and washed with 3–500 ml portions of chilled isopropyl alcohol. The tan solids were dried in a vacuum oven at 50 C.°. C.° for 16 hrs.

Dry wt=691.53 gms
Theoretical gms=1288.4 gms
Wt yld=53.7%

EXAMPLE 2

Preparation of 2-ethyl-(phenylmethyl)-1H-indol-4-ol

A. Preparation of 4-methyl-benzene sulfinic acid, anhydride 4-Methyl-benzene sulfinic acid, sodium salt, (0.9 g, 5 mmol) was suspended in benzene (5 mL). HCl (1 equiv) was added. Separately, isobutyl chloroformate (0.65 mL, 5 mmol) was added to a chilled solution of pyridine (1.2 mL, 15 mmol) in benzene (5 mL). The sulfinic acid solution was added in portions. The resultant solution was stirred for 30 min at r.t. The solvent was evaporated and the residue was partitioned between MTBE and water. The organic layer was dried over sodium sulfate, filtered and evaporated to give a colorless oil. The oil was redissolved in MTBE and washed with 0.1 N HCl solution until the pyridine was removed. After drying over sodium sulfate and filtering, the solution was evaporated to give a colorless liquid (0.30 g). $^1$H NMR (500 MHz, CDCl$_3$) □ 7.64 (d, 2 H), 7.35 (d, 2 H), 3.83 (m, 1 H), 3.37 (m, 1 H), 2.45 (s, 3 H), 1.94 (m, 3 H), 0.95 (m, 6 H).

B. Preparation of 2-ethyl-(phenylmethyl)-1H-indol-4-ol.

The starting material of Example 1B, above (0.3 g, 1.2 mmol) was dissolved in 5 mL THF. Sodium hydride (0.1 g, 2.6 mmol) was added. 4-Methyl-benzene sulfinic acid, anhydride with isobutyl hydrogen carbonate (0.3 g, 1.25 mmol) in 1 mL THF was added. The mixture was refluxed for 1 h, at which time no starting materials were observed. Continued reflux provided the product.

What is claimed is:

1. A process for preparing a compound of the formula I or a pharmaceutically acceptable salt or prodrug derivative thereof

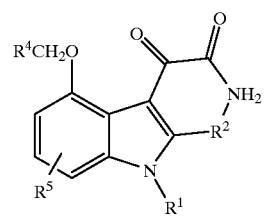

(I)

wherein:

$R^1$ is selected from the group consisting of $C_7$–$C_{20}$ alkyl;

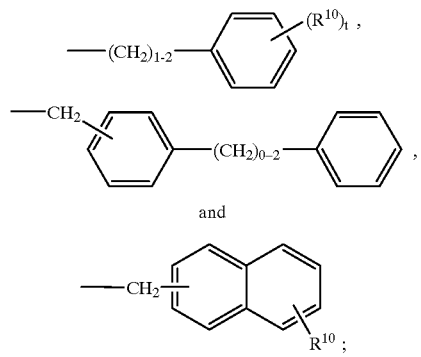

where;

$R^{10}$ is selected from the group consisting of halo, $C_1$–$C_{10}$ alkyl, $C_1$–$C_{10}$ alkoxy, —S—($C_1$–$C_{10}$ alkyl) and halo ($C_1$–$C_{10}$)alkyl, and t is an integer from 0 to 5 both inclusive;

$R^2$ is selected from the group consisting of hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), aryl, aryloxy, and HET;

$R^4$ is selected from the group consisting of —CO$_2$H, —SO$_3$H, and —P(O)(OH)$_2$ or salt or prodrug derivatives thereof; and $R^5$ is selected from the group consisting of hydrogen, ($C_1$–$C_6$)alkyl, ($C_1$–$C_6$)alkoxy, halo($C_1$–$C_6$)alkoxy, halo ($C_2$–$C_6$)alkyl, bromo, chloro, fluoro, iodo and aryl;

which process comprises the steps of a) halogenating a compound of formula X

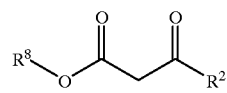
X where $R^8$ is $(C_1–C_6)$alkyl, aryl or HET;
with $SO_2Cl_2$ to form a compound of formula IX

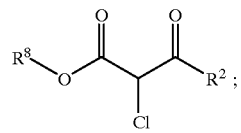
IX b) hydrolyzing and decarboxylating a compound of formula IX

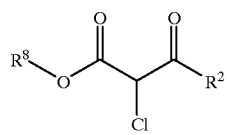
IX to form a compound of formula VIII

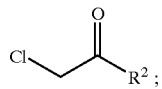
VIII c) alkylating a compound of formula VII

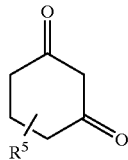
VII with a compound of formula VIII

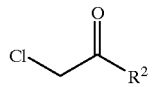
VIII to form a compound of formula VI

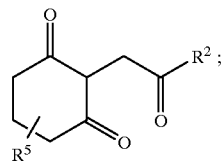
VI d) aminating and dehydrating a compound of formula VI

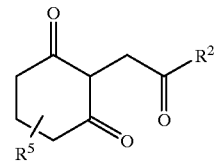
VI with an amine of the formula $R^1NH_2$ in the presence of a solvent that forms an azeotrope with water to form a compound of formula V

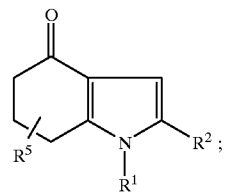
V e) oxidizing a compound of formula V

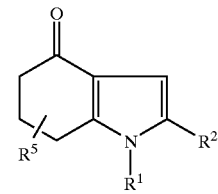
V by heating with a base and a sulfinylating reagent of the formula RSOX where R is —$(C_1–C_6)$alkyl or aryl and X is —$(C_1–C_6)$alkoxy, halo or —$OCO_2(C_1–C_6)$alkyl to form a compound of formula IV

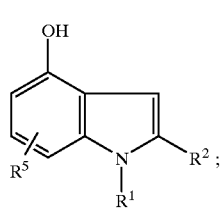
IV f) alkylating a compound of the formula IV

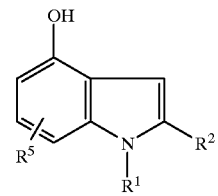
IV with an alkylating agent of the formula $XCH_2R^{4a}$ where X is a leaving group and $R^{4a}$ is —$CO_2R^{4b}$, —$SO_3R^{4b}$, —$P(O)(OR^{4b})_2$, or —$P(O)(OR^{4b})H$, where $R^{4b}$ is an acid protecting group, to form a compound of formula III

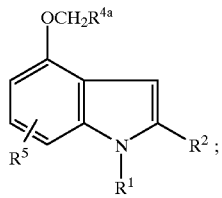

III g) reacting a compound of formula III

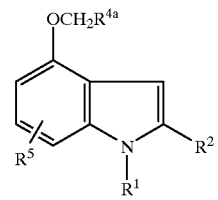

III with oxalyl chloride and ammonia to form a compound of formula II

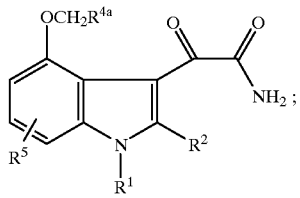

II h) optionally hydrolyzing a compound of formula II

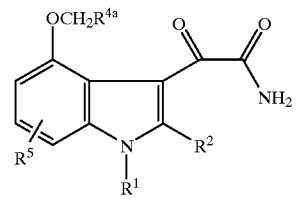

II to form a compound of formula I; and i) optionally salifying a compound of formula I.

2. A process for preparing a compound of the formula I or a pharmaceutically acceptable salt or prodrug derivative thereof

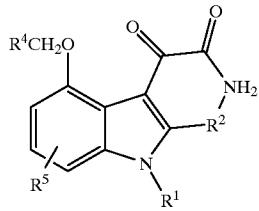

(I)

wherein:

$R^1$ is selected from the group consisting of $C_7$–$C_{20}$ alkyl;

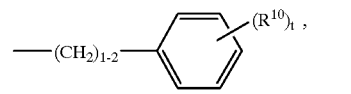

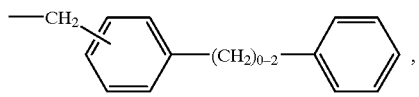

and

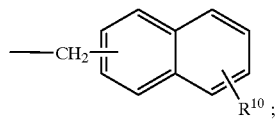

where $R^{10}$ is selected from the group consisting of halo, $C_1$–$C_{10}$ alkyl, $C_1$–$C_{10}$ alkoxy, —S—($C_1$–$C_{10}$ alkyl) and halo($C_1$–$C_{10}$)alkyl, and t is an integer from 0 to 5 both inclusive;

$R^2$ is selected from the group consisting of hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), aryl, aryloxy, and HET;

$R^4$ is selected from the group consisting of —$CO_2H$, —$SO_3H$, and —$P(O)(OH)_2$ or salt or prodrug derivatives thereof; and $R^5$ is selected from the group consisting of hydrogen, ($C_1$–$C_6$)alkyl, ($C_1$–$C_6$)alkoxy, halo($C_1$–$C_6$)alkoxy, halo($C_2$–$C_6$)alkyl, bromo, chloro, fluoro, iodo and aryl;

which process comprises the steps of e) oxidizing a compound of formula V

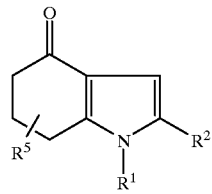

V by heating with a base and a compound of the formula RSOX where R is —($C_1$–$C_6$)alkyl or aryl and X is —($C_1$–$C_6$)alkoxy, halo or —$OCO_2(C_1$–$C_6)$alkyl to form a compound of formula IV f) alkylating a compound of the formula IV

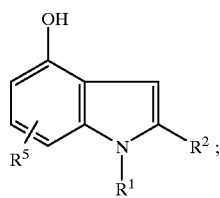

with an alkylating agent of the formula $XCH_2R^{4a}$ where X is a leaving group and $R^{4a}$ is —$CO_2R^{4b}$, —$SO_3R^{4b}$, —$P(O)(OR^{4b})_2$, or —$P(O)(OR^{4b})H$, where $R^{4b}$ is an acid protecting group, to form a compound of formula III

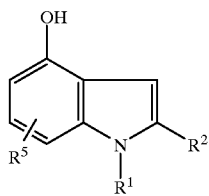

g) reacting a compound of formula III

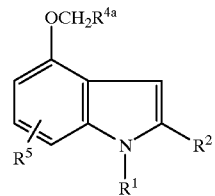

with oxalyl chloride and ammonia to form a compound of formula II

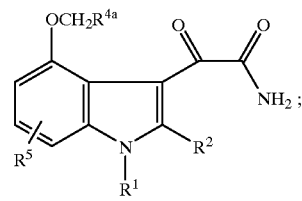

h) optionally hydrolyzing a compound of formula II

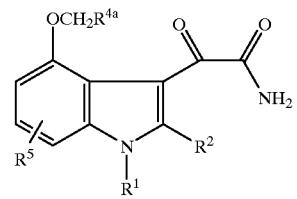

to form a compound of formula I; and i) optionally salifying a compound of formula I.

3. The process of claim 1 or 2 where the sulfinating reagent is p-tolulylsulfinicisobutyric anhydride.

4. The process of any one of claims 1 to 3 which prepares ((3-(2-amino-1,2-dioxyethyl)-2-ethyl-1-(phenylmethyl)-1H-indol-4-yl)oxy) acetic acid.

* * * * *